United States Patent [19]

Bagli et al.

[11] Patent Number: 4,469,695

[45] Date of Patent: Sep. 4, 1984

[54] 2-(4-HYDROXYALKYL-1-PIPERAZINYL)-2,4,6-CYCLOHEPTATRIEN-1-ONE DERIVATIVES

[75] Inventors: Jehan F. Bagli, Kirkland; Tibor Bögri, Montreal; Katherine Voith, Dorval, all of Canada

[73] Assignee: Ayerst, McKenna & Harrison, Inc., Montreal, Canada

[21] Appl. No.: 124,165

[22] Filed: Feb. 25, 1980

[51] Int. Cl.$^3$ .................. A61K 31/495; C07D 241/04
[52] U.S. Cl. .................................... 424/250; 544/121; 544/360; 544/362; 544/398; 544/399
[58] Field of Search ................ 424/250; 544/398, 399

[56] References Cited

PUBLICATIONS

Sianesi et al., "J. Med. Chem.", vol. 10, 1967, pp. 1144–1148.
Biggi et al., "J. Amer. Chem. Soc.", vol. 94, 1972, pp. 4700–4707.
Toda et al., "Chemical Abstracts", vol. 76, 1972, col. 72185f.
Biggi et al., "J. Amer. Chem. Soc.", vol. 95, 1973, pp. 7101–7107.
Veracini et al., "J. Chem. Soc. Commun.", 1977, pp. 623–624.
Abadir et al., "J. Chem. Soc.", 1952, pp. 2350–2353.
Nozoe et al., "Chemical Abstracts", vol. 70, 1969, col. 87244z.

*Primary Examiner*—Donald G. Daus
*Assistant Examiner*—James H. Turnipseed
*Attorney, Agent, or Firm*—Arthur E. Wilfond

[57] ABSTRACT

2-(4-Hydroxyalkyl-1-piperazinyl)-2,4,6-cycloheptatrien-1-one derivatives, therapeutically acceptable acid addition salts thereof, processes for their preparation, methods of using the derivatives and pharmaceutical compositions of the derivatives are disclosed. The derivatives exhibit dopamine-receptor stimulating activity in a mammal and are useful for treating hyperprolactinemia, galactorrhea, amenorrhea, impotence, Parkinsonism, diabetes, acromegaly, hypertension and other central nervous system disorders.

37 Claims, No Drawings

2-(4-HYDROXYALKYL-1-PIPERAZINYL)-2,4,6-CYCLOHEPTATRIEN-1-ONE DERIVATIVES

BACKGROUND OF THE INVENTION

This invention relates to novel 2-(4-hydroxyalkyl-1-piperazinyl)-2,4,6-cycloheptatrien-1-one derivatives, to therapeutically acceptable acid addition salts thereof, to a process for their preparation, to methods of using the derivatives and to pharmaceutical compositions of the derivatives. These derivatives exhibit dopamine-receptor stimulating activity in a mammal. Thus, they can be useful for treating hyperprolactinemia, galactorrhea, amenorrhea, impotence, Parkinsonism, diabetes, acromegaly, hypertension and other central nervous system disorders which respond to dopamine-receptor stimulation.

The following references were obtained from a literature search for 2-substituted tropones: E. Sianesi et al., J. Med. Chem., 10, 1144 (1967); G. Biggi et al., J. Amer. Chem. Soc., 94, 4700 (1972); T. Toda et al., Chem. Abstr., 76, 72185f (1972) for Bull. Chem. Soc. Jap., 45, 226 (1972); G. Biggi et al., J. Amer. Chem. Soc., 95, 7101 (1973); C. A. Veracini et al., J. Chem. Soc. Commun., 623 (1974); B. J. Abadir et al., J. Chem. Soc., 2350 (1952) and T. Nozoe et al., Chem. Abstr., 70, 87244z (1969) for Bull. Chem. Soc. Jap., 41, 2978 (1968). These references disclose compounds which like the compounds of this invention are 2,4,6-cycloheptatrien-1-one derivatives. Of these 2,4,6-cycloheptatrien-1-one derivatives, the 2-piperidinyl-2,4,6-cycloheptatrien-1-one described by G. Biggi et al., J. Amer. Chem. Soc., 94, 4700 (1972), cited above, can be considered the most closely related to the compounds of this invention. However, the latter 2-piperidinyl derivative is treated as a chemical curiosity without any indicated useful pharmacological activity. Furthermore, the compounds of this invention differ from the compounds of Biggi et al by having a 1-piperazinyl group at position 2 of the 2,4,6-cycloheptatrien-1-one ring.

SUMMARY OF THE INVENTION

The compounds of this invention are represented by formula I

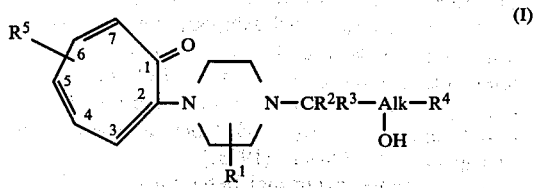

in which Alk is a trivalent alkylene having one to six carbon atoms; $R^1$ is hydrogen or lower alkyl having one to three carbon atoms; $R^2$ and $R^3$ each is hydrogen or lower alkyl having one to three carbon atoms; $R^4$ is hydrogen, phenyl, hydroxy, phenoxy, phenyl mono-, di- or trisubstituted with methylsulfonylamino, lower alkyl, halo, lower alkoxy, hydroxy or trifluoromethyl, or phenoxy mono-, di- or trisubsituted with lower alkyl, halo, lower alkoxy, hydroxy or trifluoromethyl; and $R^5$ represents a substituent at positions 3,4,5,6 or 7 of the 2,4,6-cycloheptatrien-1-one ring and is selected from hydrogen, halo, lower alkyl, lower alkoxy, trifluoromethyl, or 1-oxo(lower)alkylamino; with the proviso that when $R^4$ is hydroxy, the hydroxy groups are joined to different carbon atoms; or a therapeutically acceptable acid addition salt thereof.

A preferred group of compounds of this invention is represented by formula I in which Alk is a trivalent alkylene having one to six carbon atoms; $R^1$ is hydrogen or methyl; $R^2$ and $R^3$ each is hydrogen or lower alkyl having one to three carbon atoms, $R^4$ is hydrogen, phenyl, hydroxy, phenoxy, phenyl mono-, di- or trisubstituted with methylsulfonylamino, lower alkoxy or hydroxy, or phenoxy mono-, di- or trisubstituted with lower alkyl or halo; and $R^5$ represents a substituent at position 7 of the 2,4,6-cycloheptatrien-1-one ring and is selected from hydrogen, halo, lower alkyl, lower alkoxy, trifluoromethyl, or 1-oxo(lower)alkylamino; with the proviso that when $R^4$ is hydroxy, the hydroxy groups are joined to different carbon atoms; or a therapeutically acceptable acid addition salt thereof.

A more preferred group of compounds of this invention is represented by formula I in which Alk is a trivalent alkylene having one to three carbon atoms; $R^1$ is hydrogen; $R^2$ and $R^3$ each is hydrogen or lower alkyl having one to three carbon atoms; $R^4$ is hydrogen, phenyl, hydroxy, phenoxy, phenyl mono-, di- or trisubstituted with lower alkoxy or hydroxy or phenoxy monosubstituted with lower alkyl or halo; and $R^5$ represents a substituent at position 7 of the 2,4,6-cycloheptatrien-1-one ring and is selected from hydrogen or bromo; with the proviso that when $R^4$ is hydroxy, the hydroxy groups are joined to different carbon atoms; or a therapeutically acceptable acid addition salt thereof.

A most preferred group of compounds of this invention is represented by formula I in which Alk is CH; $R^1$, $R^2$ and $R^5$ are hydrogen; $R^3$ is hydrogen or lower alkyl having one to three carbon atoms; and $R^4$ is phenyl or phenyl mono-, di- or trisubstituted at positions 3, 4 or 5 with lower alkoxy or hydroxy; or a therapeutically acceptable acid addition salt thereof.

A pharmaceutical composition is provided by admixing the compound of formula I, or a therapeutically acceptable acid addition salt thereof, with a pharmaceutically acceptable carrier.

The compounds of this invention are used to stimulate dopamine receptors in a mammal in need thereof by administering to the mammal an effective dopamine receptor stimulating amount of a compound of formula I or a therapeutically acceptable acid addition salt thereof.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, 1-methylethyl, butyl, 1-methylpropyl, pentyl, hexyl and the like, unless stated otherwise. 1-Methylethyl and 1-methylpropyl also are known as isopropyl and sec-butyl.

The term "lower alkoxy" as used herein means straight chain alkoxy radicals containing from one to six carbon atoms and branched chain alkoxy radicals containing three or four carbon atoms and includes methoxy, ethoxy, 1-methylethoxy, butoxy, hexoxy and the like.

The term "1-oxo(lower)alkyl" or "lower alkanoyl" as used herein means straight chain 1-oxoalkyl radicals containing from two to six carbon atoms and branched chain 1-oxoalkyl radicals containing four to six carbon atoms and includes acetyl, 1-oxopropyl, 2-methyl-1-oxopropyl, 1-oxohexyl and the like.

The term "1-oxo(lower)alkoxy" as used herein means straight chain 1-oxoalkoxy radicals containing from two to six carbon atoms and branched chain 1-oxoalkoxy radicals containing four to six carbon atoms and includes acetyloxy, 1-oxopropoxy, 1-oxobutoxy, 2,2-dimethyl-1-oxopropoxy, 1-oxohexoxy and the like.

The term "halo" as used herein means halogens and includes fluorine, chlorine, bromine and iodine, unless stated otherwise.

The term "—Alk—" as used herein means a trivalent alkyl radical derived from a straight and branched chain aliphatic hydrocarbons containing from one to six carbon atoms by removal of three hydrogen atoms, unless stated otherwise, and includes, for example

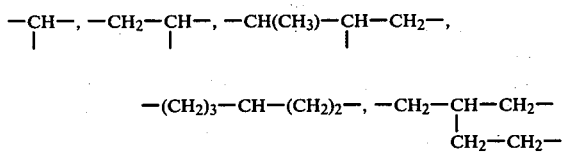

The term

as used herein means a divalent alkanone radical derived from straight and branched chain alkanones having one to six carbon atoms by removal of two hydrogen atoms, unless stated otherwise, and includes, for example,

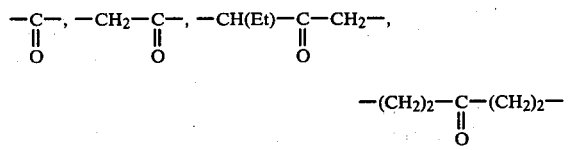

and the like.

The term "lower alkanol" as used herein means both straight and branched chain alkanols containing from one to four carbon atoms and includes methanol, ethanol, isopropanol, butanol and the like.

The term "organic proton acceptor" as used herein means the organic bases, or amines for instance, triethylamine, pyridine, N-ethyl-morpholine, 1,5-diazabicyclo[4.3.0]non-5-ene and the like.

The term "inorganic proton acceptor" as used herein means the inorganic bases, preferably the alkali metal hydroxides, carbonates and bicarbonates, for example, sodium hydroxide, potassium hydroxide, sodium carbonate, sodium bicarbonate, potassium carbonate and the like.

The term "proton acceptor" as used herein means a proton acceptor selected from an organic proton acceptor and inorganic proton acceptor, as defined herein.

The compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Examples of suitable acids to form these salts include: the common mineral acids, e.g., hydrohalic, sulfuric or phosphoric acids; the organic acids, e.g., formic, acetic, maleic, malic, citric, or tartaric acid; and acids which are sparingly soluble in body fluids and which impart slow-release properties to their respective salts, e.g., pamoic acid, tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The discovery in the mid-1960's of two major dopamine (DA) systems indicated that this neurotransmitter exerted control over a number of physiological functions. Against this background an interest arose to develop DA receptor agonists to study the function of the dopaminergic systems and to evaluate these agonists as possible therapeutic agents in Parkinsons's disease and certain neuroendocrine disorders, for example, hyperprolactinemia, galactorrhea, amenorrhea, impotence, hypertension and other central nervous system disorders.

The DA receptor agonists exert a variety of pharmacological effects, some of the most characteristic being the ones that occur in animals in which DA deficiency is brought about to mimic the Parkinsonian syndrome. An important model was developed by U. Ungerstedt, Acta. Physiol. Scand., Suppl. 367, 69–93 (1971) who, by means of unilateral injections of 6-hydroxydopamine (6-OHDA) into the DA pathway, could produce selective lesions of the ascending DA pathways on one side of the brain. Ungerstedt (1971) demonstrated in these lesioned rats that DA receptor agonists induced rotational behavior towards the innervated side. The response is due to the development of receptor supersensitivity in the denervated striatum resulting in a higher degree of DA receptor activity on the denervated- as compared to the innervated-side after treatment with DA receptor agonists. Due to this imbalance between the two sides, a rotational behavior is elicited, the direction being always towards the less activated side. It is of interest that in the discovery of the DA receptor stimulating properties of bromocriptine, the 6-OHDA rotational model was utilized [H. Corrodi et al., J. Pharm. Pharmacol., 25, 409–412 (1973)].

In the test for rotational behavior in rats following the unilateral 6-OHDA-induced destruction of one nigrostriatal pathway, the method described by C. J. Pycock and C. D. Marsden, Europ. J. Pharmacol., 47, 167 (1978) was followed. The rats (230–250 g) were anesthetized with sodium pentobarbital (40 mg/kg i.p.) and intracerebral injections were made using a Stoelting stereotaxic instrument, (C. H. Stoelting Co., Chicago, Ill., U.S.A.). Unilateral injections of 6-OHDA hydrobromide (8 µg/3 µl delivered at a rate of 1 µl per min) were made into the ascending median forebrain bundle (MFB) in the lateral hypothalamus according to the coordinates of the De Groot brain atlas, J. De Groot, Verhandel, Koninkl. Ned. Akad. Wetenschap. Natuurk. 52: 1–40 (1959), (A: +4.6, L: ±1.9, V: −2.7). 6-OHDA was made up in ice-cold distilled water containing 0.2 mg/ml ascorbic acid.

Three weeks after operation, the rats were tested for rotational behavior in response to apomorphine hydrochloride (0.25 mg/kg, s.c.). Rats which consistently showed more than 5 turns/min after apomorphine were selected and the compound of formula I was then administered. The rat was immediately placed in the rotometer, described by K. Voith and J. R. Cummings, Can. J. Pharmacol., 54, 551 (1976), and the rotation was continuously recorded until drug effect subsided. By using this test, the following compound of formula I is an effective dopamine receptor agonist (the amount of the compound, route of administration and total turns±S.E. (standard error) during the time observed are indicated in the parenthesis): 2-[4-[2-hydroxy-2-(3,4-dimethoxyphenyl)ethyl]-1-piperazinyl]-2,4,6-cycloheptatrien-1-one (described in Example 4, at a subcutaneous dose of 5 mg/kg exhibited 2233±607 turns in a four hour duration) and 2-[4-[2-hydroxy-2-(3,4-dimethoxyphenyl)ethyl]-1-piperazinyl]-2,4,6-cycloheptatrien-1-one hydrochloride (described in Example 4, at an oral dose of 10 mg/kg exhibited 1649±298 turns in a six hour duration and at an oral dose of 20 mg/kg exhibited 5167±1065 turns in an eight hour duration).

A recently developed animal model, described by G. P. Smith and R. C. Young in "Advances in Neurology", Vol. 5, F. H. McDowell and A. Barbeau, Eds., Raven Press, New York, pp. 427–432 (1974), shows that rats exhibit almost complete akinesia in an open field following the bilateral injection of 6-OHDA into the anterolateral hypothalamus. The troponylpiperazines of formula I are able to reverse this 6-OHDA-induced hypokinesia and as a result, function as dopamine receptor agonists. In this test for dopamine receptor agonists, the compounds of formula I exhibit a pharmacological response that is quantitatively comparable to that of apomophine and bromocriptine.

Experiments were performed on male Sprague-Dawley rats housed in air-conditioned quarters. The room was lighted between 0700 and 1900 hr daily and was maintained at a temperature of 24° C.±2° C.

The method of Smith and Young, cited above, was followed. Rats (approximately 280 g) were operated on under sodium pentobarbital anesthesia. Using a Stoelting stereotaxic instrument, the tip of a 26 gauge cannula was positioned in the anterolateral hypothalamus (7 mm anterior to the interaural line, 2 mm lateral to the midline and 8 mm below the dura) according to the De Groot brain atlas, noted above. Via a polyethylene tubing (PE 20) the cannula was connected to a 10 μl syringe which was mounted in a Starrett micrometer head drive, C. H. Stoelting Co., Chicago, Ill., U.S.A. All injections were bilateral. Each injection consisted of 4 μl of distilled water containing 6-OHDA (6.5 μg base/μl) and ascorbic acid (0.4 μg/μl).

The animals had free access to Purina Laboratory Chow pellets and tap water. However since anterolateral hypothalamic 6-OHDA injections produce aphagia and adipsia, intragastric feeding was necessary in order to prevent drastic weight loss. The rats received a daily gastric intubation of 2 g of the "modified rat tube feeding diet" (ICN Pharmaceuticals, Inc., Cleveland, Ohio, U.S.A.) mixed with approximately 2 ml tap water.

Ambulation in the open field was evaluated in an apparatus consisting of a wooden box (69 cm×69 cm×42 cm) with an arborite floor. The floor was divided into 36 squares (11.5 cm×11.5 cm). The placement of all four limbs in one square was taken as one ambulation score.

In the present experiments all compounds were evaluated four days after the intracerebral injection of 6-OHDA. The rat was placed into the center of the open field and observed for a 2-min period. Only rats with almost total akinesia were used. Apomorphine bromocriptine or the compounds of formula I were injected s.c. to groups of 4–12 rats. Subsequently, the number of squares were counted which the animal entered during several 2-min observation periods. Apomorphine was evaluated at 5, 10, 15, 20 and 30 min; bromocriptine at 2, 3, 4, 5, 6 and 7 hr; and the compounds of formula I at 15, 30, 45, 60, 90 and 120 min after injection. Each animal was used only once. The results are expressed as cumulative number of ambulation scores which are the sums of the scores obtained during the 2-min observation periods.

The following substances were used; apomorphine hydrochloride (Macfarlan Smith Ltd., Edinburgh, Scotland), bromocriptine (CB-154) (Sandoz Pharmaceuticals, East Hanover, N.J., U.S.A.) and 6-OHDA hydrobromide (Aldrich Chemical Co., Inc., Milwaukee, Wis., U.S.A.). The compounds were dissolved in distilled water or suspended in distilled water with a few drops of polysorbate 80 (Tween 80; "Tween" is a registered trade mark). If the compound was an oil, 0.4 ml of dimethyl sulfoxide was added. Solutions were prepared fresh on the day of the experiment. The 6-OHDA solution was kept in ice throughout the injection procedure. All doses refer to the base.

Using the above described method, apomorphine at a dose of 0.5 mg/kg exhibited a score of 135±41 and bromocriptine at a dose of 10 mg/kg exhibited a score of 112±23. Similarly, the following representative compounds of formula I are effective dopamine receptor agonists (the amount of the compound and its cumulative ambulation score are indicated in the parentheses): 4-(2-oxo-3,5,7-cycloheptatrien-1-yl)-1-piperazineethanol (described in Example 1, at a dose of 50 mg/kg exhibited a score of 187±35), 2-[4-(3-hydroxypropyl)-1-piperazinyl]-2,4,6-cycloheptatrien-1-one (described in Example 3, at a dose of 50 mg/kg exhibited a score of 71±10), and 2-[4-[2-hydroxy-2-(3,4-dimethoxyphenyl)ethyl]-1-piperazinyl]-2,4,6-cycloheptatrien-1-one (described in Example 4, at a dose of 10 mg/kg exhibited a score of 191±47).

Furthermore, the intermediate ketones of formula VII, described hereinafter, also exhibit dopamine-receptor stimulating activity in a mammal in a manner similar to the compounds of formula I. For example, in the latter test for testing dopamine receptor agonists, the following compound of formula VII is an effective dopamine receptor agonist; 2-[4-(2-oxopropyl)-1-piperazinyl]-2,4,6-cycloheptatrien-1-one (described in Example 6, at a dose of 50 mg/kg exhibited a score of 65±13).

The above described test method for dopamine receptor agonists shows that the compounds of formula I are active as dopamine receptor agonists. The compounds, thus, can be used clinically in the treatment of hyperprolactinemia, galactorrhoea, amenorrhoea, impotence, diabetes, Parkinsonism, acromegaly, hypertension and other central nervous system disorders which respond to dopaminereceptor stimulation.

The compounds of formula I of this invention are used alone or in combination with pharmacologically acceptable carriers, the proportion of which is determined by the solubility and chemical nature of the compound, chosen route of administration and standard biological practice. For example, they are administered orally in solid form i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as dopamine receptor agonists will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. For example, the effective dopamine receptor stimulating amount of the compounds for i.p. administration usually ranges from about 0.1 mg to about 250 mg per kilogram body weight per day in single or divided doses although as aformentioned variations will occur. However a dosage level that is in the range of from about 1.0 to about 100 mg per kilogram body weight per day in single or divided doses is employed most desirably for i.p. administration in order to achieve effective results. For oral administration, effective amounts can range from about 1.0 to about 250 mg per kilogram body weight per day in single or divided doses preferably about 5.0 to 100 mg per kilogram body weight per day.

The compound of formula I, or a therapeutically acceptable salt thereof, also can be used to produce beneficial effects in the treatment of Parkinsonism, hyperprolactinemia and related disorders when combined with a therapeutically effective amount of an agent commonly used in the treatment of Parkinsonism, hyperprolactinemia and related disorders. Such agents include, for example, apomorphine and its derivatives, piribedil and its derivatives, dopaminergic ergot derivatives, especially bromocriptine and lergotrile, 2-amino-6,7-dihydroxy-(1,2,3,4)-tetrahydronaphthalene (ADTN), levodihydroxyphenylalanine (levodopa), combination of levodopa with carbidopa, L-prolyl-L-leucylglycinamide (MIF) and its derivatives, especially L-prolyl-N-methyl-D-leucylglycinamide (pareptide), biperiden, cycrimine hydrochloride, procyclidine, trihexyphenidyl hydrochloride, benztropine mesylate, chlorphenoxamine hydrochloride, diphenhydramine hydrochloride, orphenadrine hydrochloride, ethopropazine hydrochloride and the enzymes, monoamine oxidase B and catechol-O-methyl transferase. A combination of the foregoing agents can be substituted for a single agent. Suitable methods of administration, compositions and dosages of the agents are well known in the art; for instance, "Physician Desk Reference", 32 ed., Medical Economics Co., Oradell, N.J., U.S.A., 1978. When used in combination, the compound of formula I, or its therapeutically acceptable salt, is administered as described previously.

PROCESS

Reaction scheme 1 illustrates methods for preparing a number of the compounds of formula I.

REACTION SCHEME 1

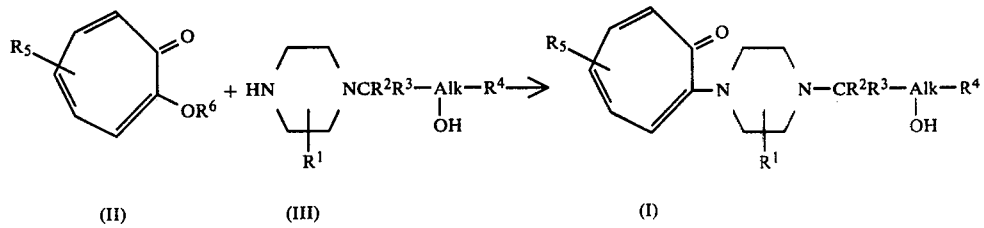

(II)　　　(III)　　　(I)

-continued
REACTION SCHEME 1

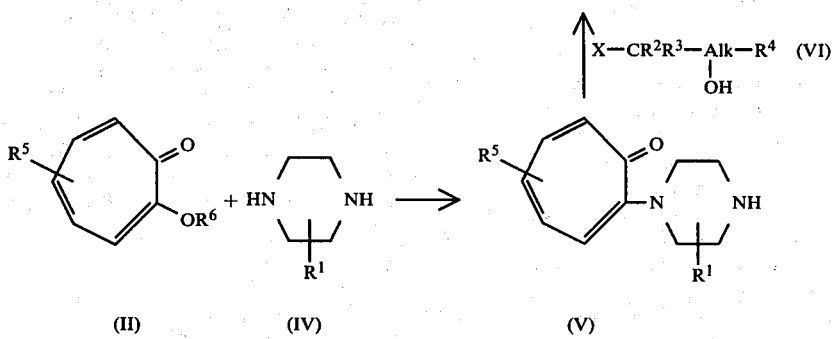

(II)        (IV)                    (V)

The 2-alkoxy-tropones, of formula II in which $R^5$ represents a substituent at positions 3,4,5,6 or 7 of the 2,4,6-cycloheptatrien-1-one ring and is selected from hydrogen, halo, lower alkyl, lower alkoxy, trifluoromethyl, or 1-oxo(lower)alkylamino; and $R^6$ is lower alkyl, suitable as starting materials, are described in a number of reports; for example, see the review on tropone derivatives, their preparation and their interconversions by F. Pietra, Chem. Rev., 73, 293 (1973). Thus, the 2-alkoxy-tropones are either known or they can be prepared by conventional means.

Also, the piperazine and piperazine derivatives of formulae III and IV are either known, commercially available or can be prepared by conventional means. For example, one useful method of preparing a compound of formula III, the appropriate nitrogen of the piperazine of formula IV wherein $R^1$ is as defined herein is first protected with an amino protecting group, for instance benzyl, formyl, tert-butoxycarbonyl and the like. The desired

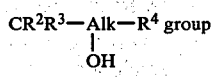

is then introduced onto the other nitrogen of this protected piperazine; various methods of introducing this group are described hereinafter. Subsequent removal of the protecting group, for example, hydrogenation in the case of benzyl, gives the corresponding piperazine derivative of formula III.

With reference to reaction scheme 1, the 2-alkoxy-tropone of formula II in which $R^5$ is as defined herein and $R^6$ is lower alkyl, preferably methyl or ethyl, is condensed with the piperazine derivative of formula III in which Alk is as defined herein; $R^1$ is hydrogen or lower alkyl; $R^2$ and $R^3$ each is hydrogen or lower alkyl having one to three carbon atoms; and $R^4$ is hydrogen, phenyl, hydroxy, phenoxy, phenyl mono-, di- or trisubstituted with methylsulfonylamino, lower alkyl, halo, lower alkoxy, hydroxy or trifluoromethyl, or phenoxy mono-, di- or trisubstituted with lower alkyl, halo, lower alkoxy, hydroxy or trifluoromethyl; with the proviso that when $R^4$ is hydroxy, the hydroxy groups are joined to different carbon atoms to obtain the corresponding compound of formula I in which Alk, $R^1$, $R^2$, $R^3$ and $R^5$ are as defined herein and $R^4$ is as defined immediately above. The condensation is readily effected by heating a solution of the compound of formula II with one to five, preferably 1.3 to 2.0, molar equivalents of the piperazine of formula III in an inert organic solvent, for example, a lower alkanol, benzene, chloroform, acetonitrile, toluene and the like, preferably methanol or ethanol, at 50° to 100° C. for 10 to 60 hours and isolating the corresponding compound of formula I.

The above described condensation of the compounds of formula II and formula III is especially useful for preparing the compounds of formula I in which Alk, $R^1$, $R^2$, $R^3$ and $R^5$ are as defined herein and $R^4$ is hydrogen.

Condensation of the compound of formula II and the piperazine of formula IV, in the same manner as described above for the compounds of formulae II and III, gives the corresponding compound of formula V in which $R^1$ and $R^5$ are as defined herein. The compound of formula V is condensed in the presence of a proton acceptor with a halide of formula VI wherein X is bromo, chloro or iodo; Alk is as defined herein; $R^2$ and $R^3$ each is hydrogen or lower alkyl having one to three carbon atoms; $R^4$ is hydrogen, phenyl, phenoxy, phenyl mono-, di- or trisubstituted with methylsulfonylamino, lower alkyl, halo, lower alkoxy, hydroxy or trifluoromethyl, or phenoxy mono-, di- or trisubstituted with lower alkyl, halo, lower alkoxy, hydroxy or trifluoromethyl; with the provisio that when $R^4$ is hydroxy, the hydroxy groups are joined to different carbon atoms to obtain the corresponding compound of formula I in which Alk, $R^1$, $R^2$, $R^3$ and $R^5$ are as defined herein and $R^4$ is as defined immediately above. About one to ten, preferably 1.0 to 1.5, molar equivalents of the proton acceptor and about one to five, preferably 1.0 to 1.5, molar equivalents of the halide of formula VI are usually used. For this condensation, suitable proton acceptors can be selected from organic and inorganic proton acceptors, for example triethylamine, pyridine, N-ethylmorpholine, sodium bicarbonate, sodium or potassium carbonate, sodium or potassium lower alkoxide and the like. Sodium or potassium carbonate is the preferred proton acceptor. Usually the condensation is conducted in an inert organic solvent, for example, benzene, toluene, dichloromethane, chloroform, lower alkanol, acetonitrile, dimethylformide, acetone and the like. Acetonitrile and/or methanol is the preferred solvent for the condensation. To achieve the condensation, the reaction mixture is maintained at 20° to 85° C. for three hours to three days and the compound of formula I is isolated.

The latter conditions are also useful for the condensation of the compound of formula V in which $R^1$ and $R^5$ are as defined herein with an epoxide of formula

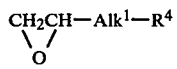

wherein $Alk^1$ is a divalent lower alkyl having one to five carbon atoms and $R^4$ is hydrogen, phenyl, hydroxy, phenoxy, phenyl mono-, di- or trisubstituted with methylsulfonylamino, lower alkyl, halo, lower alkoxy, hydroxy or trifluoromethyl, or phenoxy mono-, di- or trisubstituted with lower alkyl, halo, lower alkoxy, hydroxy or trifluoromethyl to give the corresponding compound of formula I in which $R^1$ and $R^5$ are as defined herein; $R^2$ and $R^3$ are hydrogen, Alk is $CH(OH)-Alk^1$ wherein $Alk^1$ is a divalent lower alkyl having one to five carbon atoms and $R^4$ is as defined immediately above.

Similarly, condensation of the compound of formula V in which $R^1$ and $R^5$ are as defined herein with about one to two molar equivalents of a chloroepoxide of the formula

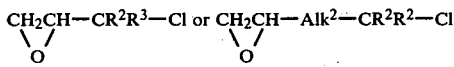

wherein $Alk^2$ is a divalent lower alkyl having one to four carbon atoms and $R^2$ and $R^3$ are as defined herein in the presence of about 1.4 to 1.9 molar equivalents of a proton acceptor, preferably potassium carbonate, in an inert organic solvent, preferably acetonitrile, at 60° to 85° C. for 30 to 60 hours gives the corresponding compound of formula I in which $R^1$, $R^2$, $R^3$ and $R^5$ are as defined herein; $R^4$ is hydroxy and

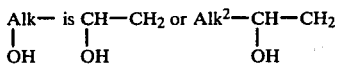

wherein $Alk^2$ is as defined herein, respectively.

Reaction of the compound of formula V in which $R^1$ and $R^5$ are as defined herein with 1.5 to 3.0 molar equivalents of ethylene oxide in methanol at about 0° C. for about 10 to 30 hours gives the corresponding compound of formula I in which Alk is CH, $R^1$ and $R^5$ are as defined herein; and $R^2$, $R^3$ and $R^4$ are hydrogen.

Another method of preparing the compounds of formula I in which Alk, $R^1$, $R^2$, $R^3$ and $R^5$ are as defined herein and $R^4$ is hydrogen, hydroxy, phenyl, phenoxy, phenyl mono-, di- or trisubstituted with methylsulfonylamino, lower alkyl, halo, lower alkoxy, hydroxy or trifluoromethyl, or phenoxy mono-, di- or trisubstituted with lower alkyl, halo, lower alkoxy, hydroxy or trifluoromethyl involves the reaction of the compound of formula V in which $R^1$ and $R^5$ are as defined herein with about 1.1 to 1.5 molar equivalents of a proton acceptor, preferably potassium carbonate, and about one molar equivalent of an alkanone of the formula

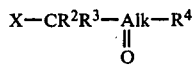

wherein X is bromo, chloro or iodo; Alk, $R^2$ and $R^3$ are as defined herein, and $R^4$ is hydrogen, hydroxy, phenyl, phenoxy, phenyl mono-, di- or trisubstituted with methylsulfonylamino, lower alkyl, halo, lower alkoxy, hydroxy or trifluoromethyl, or phenoxy mono-, di- or trisubstituted with lower alkyl, halo, lower alkoxy, hydroxy or trifluoromethyl, with the proviso that when $R^4$ is hydroxy, the hydroxy and ketone groups are joined to different carbon atoms, in an inert organic solvent, preferably acetonitrile, at 50° to 90° C. for one to ten hours to obtain the corresponding intermediate ketone of formula VII in which $R^1$, $R^2$, $R^3$, $R^5$ and Alk are as defined herein and $R^4$ is as defined immediately above. Reduction of this intermediate with five to ten molar equivalents of a reducing agent, preferably sodium borohydride, in an inert organic solvent preferably

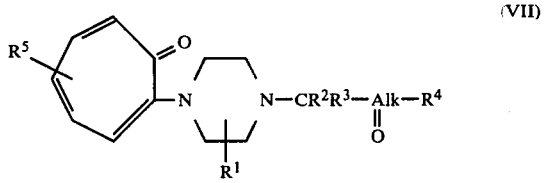

a mixture of methanol and chloroform, at 10° to 30° C. for one-half to ten hours gives the corresponding compound of formula I in which Alk, $R^1$, $R^2$, $R^3$ and $R^5$ are as defined herein and $R^4$ is hydrogen, hydroxy, phenyl, phenoxy, phenyl mono-, di- or trisubstituted with methylsulfonylamino, lower alkyl, halo, lower alkoxy, hydroxy or trifluoromethyl, or phenoxy mono-, di- or trisubstituted with lower alkyl, halo, lower alkoxy, hydroxy or trifluoromethyl, with the proviso that when $R^4$ is hydroxy, the hydroxy groups are joined to different carbon atoms.

The following examples illustrate further this invention.

EXAMPLE 1

4-(2-Oxo-3,5,7-cycloheptatrien-1-yl)-1-piperazine-ethanol (I: $R^1$, $R^2$, $R^3$, $R^4$ and $R^5$=H and Alk=CH)

A mixture of 1-(2-hydroxyethyl)piperazine (10.0 g) and 2-methoxy-2,4,6-cycloheptatrien-1-one (10.9 g) in methanol (50 ml) was refluxed for 24 hr and evaporated. The residue was chromatographed on silica gel (100 g) using methanol-ethyl acetate (1:4). The eluates were evaporated and crystallized from ethyl acetate-hexane to give the title compound (9.2 g): mp 85°–86° C.; ir (CHCl$_3$) 3440, 1616 and 1555 cm$^1$; nmr(CDCl$_3$) δ2.55 (t, 2H), 2.63 (m, 4H), 3.30 (m, 4H), 3.60 (t, 2H) and 6.40–7.65 (m, 5H); and Anal. Calcd for $C_{13}H_{18}N_2O_2$: C, 66.64% H, 7.74% N, 11.96% and Found: C, 66.12% H, 7.83% N, 11.99%.

Similarly, by condensing 1-(2-hydroxyethyl)piperazine with 5-chloro-2-methoxy-2,4,6-cycloheptatrien-1-one or 7-bromo-2-methoxy-2,4,6-cycloheptatrien-1-one, the following compounds of formula I were obtained respectively: 5-chloro-2-[4-(2-hydroxyethyl)-1-piperazinyl]-2,4,6-cycloheptatrien-1-one (I: $R^1$, $R^2$, $R^3$ and $R^4$=H, $R^5$=5—Cl and Alk=CH): ir(CHCl$_3$) 3450 and 1563 cm$^{-1}$; uv max (MeOH) 259 (ε=12300) and 235 nm (ε=10340); and nmr (CDCl$_3$) δ2.2 (s, 1H), 2.7 (m, 6H), 3.4 (t, 4H), 3.65 (t, 2H,) and 7.0 (m, 4H); and 7-bromo-2-[4-(2-hydroxyethyl)-1-piperazinyl]-2,4,6-cycloheptatrien-1-one hydrobromide (I: $R^1$, $R^2$, $R^3$ and $R^4$=H, $R^5$=7—Br and Alk=CH): mp 214°–215° C. (crystallized from ethyl acetate-methanol); ir(mull) 3350, 2700 and 1577 cm$^1$; uv max(MeOH) 252 (ε=17260) and 221 nm (ε=18760); nmr(DMSO-d$_6$) δ3.4 (m, 12H), 5.2 (s, 1H) and 7.0–8.15 (m, 5H); and Anal.

Calcd for $C_{13}H_{17}N_2O_2HBr$: C, 39.61% H, 4.60% N, 7.10% and Found: C, 39.83% H, 4.65% N, 7.31%.

EXAMPLE 2

2-(1-Piperazinyl)-2,4,6-cycloheptatrien-1-one (V: $R^1$ and $R^5$=H)

A solution of 2-methoxy-2,4,6-cycloheptatrien-1-one (136 g) and piperazine (136 g) in methanol (250 ml) was refluxed for 4 hr and the reaction vessel was placed in an ice bath. Water (150 ml), then acetic acid was slowly added until the solution was acidic. The mixture was filtered and the filtrate was evaporated and chromatographed on silica gel using chloroform-acetone (1:1) and then with acetic acid-methanol (1:4). The eluates from the latter solvent were evaporated to give an oil of the acetate salt (153 g) of the title compound.

Alternatively, the reaction solution was cooled to induce crystallization of the dimer and filtered. The filtrate was diluted with acetone to 1000 ml and a solution of methane sulfonic acid (106 g) in acetone (250 ml) was added to the filtrate in an ice bath. The precipitate was collected and washed with acetone and diethyl ether to give 146 g of the methane sulfonate salt of the title compound: mp 174°–176° C.; ir(mull) 2900, 1563 and 1180 cm$^{-1}$; uv max(MeOH) 343 ($\epsilon$=8910), 252 ($\epsilon$=13110) and 223 nm ($\epsilon$=11250); nmr(DMSO-d$_6$) $\delta$2.35 (s, 3H), 3.35 (m, 8H), 6.95 (m, 5H) and 8.8 (broad, 2H); and Anal. Calcd for $C_{11}H_{14}N_2O.CH_3SO_3H$: C, 50.32% H, 6.33% N, 9.80% and Found: C, 50.06% H, 6.39% N, 9.44%.

EXAMPLE 3

2-[4-(3-Hydroxypropyl)-1-piperazinyl)-1-piperazinyl]-2,4,6-cycloheptatrien-1-one (I: $R^1$, $R^2$, $R^3$, $R^4$ and $R^5$=H and Alk=CH$_2$CH)

A mixture of 2-(1-piperazinyl)-2,4,6-cycloheptatrien-1-one acetate (15.5 g, described in Example 2), 3-bromopropanol (10.5 g) and potassium carbonate (13.8 g) in acetonitrile (150 ml) was stirred at room temperature for 16 hr, diluted with water (50 ml) and extracted with chloroform. The chloroform extract was dried and evaporated. The residue (16.0 g) was chromatographed on silica gel (500 g) using methanol-acetone (1:1). After evaporation of the eluate, the residue was crystallized from ethyl acetate-hexane to give 1.38 g of the title compound: mp 98°–100° C.; ir(CHCl$_3$) 3260 and 1565 cm$^{-1}$; uv max (MeOH) 350 ($\epsilon$=9410), 255 ($\epsilon$=14180) and 227 nm($\epsilon$=11470); nmr(CDCl$_3$) $\delta$1.75 (m, 2H), 2.65 (m, 6H), 3.5 (m, 7H) and 6.81 (m, 5H); and Anal. Calcd for $C_{14}H_{20}N_2O_2$: C, 67.71% H, 8.12% N, 11.28% and Found: C, 67.38% H, 8.38% N, 11.08%. In the same manner but replacing 3-bromopropanol with an equivalent amount of 3-[4-(1,1-dimethylethyl)phenoxy]-1,2-epoxypropane, 3-(4-chlorophenoxy)-1,2-epoxypropane, 2-bromopropanol or 3-bromo-1,2-propandiol, the following compounds of formula I were obtained respecitvely: 2-[4-[3-[4-(1,1-dimethylethyl)phenoxy]-2-hydroxypropyl]-1-piperazinyl]-2,4,6-cycloheptatrien-1-one (I: $R^1$, $R^2$, $R^3$ and $R^5$=H; $R^4$=4-(1,1-dimethylethyl)phenoxy; and Alk=CHCH$_2$): mp 88°–90° C. (crystallized from ethyl acetate-hexane); ir(mull) 3300, 1560 and 1250 cm$^{-1}$; uv max(MeOH) 352 ($\epsilon$=7420), 280 ($\epsilon$=5520), 257 ($\epsilon$=11720) and 223 nm($\epsilon$=21680); nmr(CDCl$_3$) $\delta$1.3 (s, 9H), 2.7 (m, 6H), 3.35 (t, 4H), 4.00 (m, 3H) and 7.00 (m, 9H); and Anal. Calcd for $C_{24}H_{32}N_2O_3$: C, 72.69% H, 8.14% N, 7.07% and Found: C, 72.98% H, 8.21% N, 7.01%; 2-[4-[3-(4-chlorophenoxy)-2-hydroxypropyl]-1-piperazinyl]-2,4,6-cycloheptatrien-1-one (I: $R^1$, $R^2$, $R^3$ and $R^5$=H; $R^4$=4-chlorophenoxy and Alk=CHCH$_2$): mp 110°–112° C. (crystallized from ethyl acetate-hexane); ir(CHCl$_3$) 3570, 3410 and 1560 cm$^{-1}$; uv max(MeOH) 353 ($\epsilon$=9950), 256 ($\epsilon$=15360) and 227 nm($\epsilon$=24710); nmr(CDCl$_3$) $\delta$2.70 (m, 6H), 3.35 (t, 4H), 4.00 (m, 3H) and 6.90 (m, 9H); and Anal. Calcd for $C_{20}H_{23}ClNO_3$: C, 64.07% H, 6.18% N, 7.47% and Found: C, 63.37% H, 6.19% N, 7.31%; 2-[4-[1-(hydroxymethyl)ethyl]-1-piperazinyl]-2,4,6-cycloheptatrien-1-one (Z)-2-butenedioate (I: $R^1$, $R^2$, $R^4$ and $R^5$=H; $R^3$=CH$_3$; and Alk=CH): mp 115°–116° C. (crystallized from methanol-diethyl ether); ir(CHCl$_3$) 3670, 3320, 1705 and 1570 cm$^{-1}$; uv max(MeOH) 342 ($\epsilon$=9505) and 250 nm($\epsilon$=15975); nmr(CDCl$_3$) $\delta$1.35 (d, 3H), 3.6 (m, 11H), 6.2 (s, 2H), 7.0 (m, 5H) and 11.0 (m, 3H); and Anal. Calcd for $C_{14}H_{20}N_2O_2.C_4H_4O_4$: C, 59.32% H, 6.64% N, 7.69% and Found: C, 59.11% H, 6.72% N, 7.63% and 2-[4-(2,3-dihydroxypropyl)-1-piperazinyl]-2,4,6-cycloheptatrien-1-one (I: $R^1$, $R^2$, $R^3$ and $R^5$=H; $R^4$=OH; and Alk=CHCH$_2$): mp 11°–112° C. (crystallized from ethyl acetate-hexane); ir (CHCl$_3$) 3580, 3420 and 1565 cm$^{-1}$; uv max (MeOH) 351 ($\epsilon$=9700), 255 ($\epsilon$=14500) and 221 nm($\epsilon$=11400); nmr(CDCl$_3$) $\delta$2.6 (m, 6H), 3.5 (s, 1H), 3.35 (t, 4H), 3.65 (m, 3H) and 6.8 (m, 5H); and Anal. Calcd for $C_{14}H_{20}N_3O_3$: C, 63.61% H, 7.62% N, 10.60% and Found: C, 63.43% H, 7.87% N, 10.55%.

EXAMPLE 4

2-[4-[2-Hydroxy-2-(3,4-dimethoxyphenyl)ethyl]-1-piperazinyl]-2,4,6-cycloheptatrien-1-one (I: $R^1$, $R^2$, $R^3$ and $R^5$=H; $R^4$=3,4-dimethoxyphenyl; and Alk=CH)

A solution of bromine (30.6 g, 1.2 eg) in chloroform (150 ml) was added dropwise to a solution of 1-(3,4-dimethoxyphenyl)-1-ethanone (28.8 g) in chloroform (50 ml) over a period of 3–5 hr. The mixture was stirred for 1.5 hr. A stream of nitrogen was passed to remove the hydrobromic acid gas. The mixture was diluted with chloroform, washed with water, aqueous sodium bicarbonate and water, dried and evaporated. The crude product (48.3 g) was passed through a silica gel column (1.5 kg) using ethyl acetate-hexane (1:4) and the eluates were evaporated to give 2-bromo-1-(3,4-dimethoxyphenyl)-1-ethanone (19.7 g), mp 87°–90° C.

Similarly, by replacing 1-(3,4-dimethoxyphenyl)-1-ethanone with 1-[4-(methylsulfonylamino)phenyl]-1-ethanone, 1-phenyl-1-ethanone, 1-(3,4-dimethoxyphenyl)-1-propanone, 1-(3,4,5-trimethoxyphenyl)-1-ethanone, 1-(4-methoxyphenyl)-1-ethanone, 2-butanone or 1-(4-fluorophenyl)-1-ethanone, the following compounds are obtained respectively: 2-bromo-1-[4-(methylsulfonylamino)phenyl]-1-ethanone, mp 185°–190° C. (crystallized from methanol); 1-phenyl-2-bromo-1-ethanone, 2-bromo-1-(3,4-dimethoxyphenyl)-1-propanone, 2-bromo-1-(3,4,5-trimethoxyphenyl)-1-ethanone, 2-bromo-1-(4-methoxyphenyl)-1-ethanone, 2-bromo-2-butanone and 2-bromo-1-(4-fluorophenyl)-1-ethanone.

To a suspension of 2-(1-piperazinyl)-2,4,6-cycloheptatrien-1-one methane sulfonate (19.64 g, described in Example 2) in acetonitrile, (150 ml) was added potassium carbonate (20.8 g). The resulting suspension was refluxed for about 20 min. A solution of 2-bromo-1-(3,4-dimethoxyphenyl)-1-ethanone (17.8 g) in acetonitrile (100 ml) was added dropwise. The mixture was stirred at 85° C. for 1.25 hr. The mixture was filtered and the filtrate was evaporated. The filtered solid and oily residue was taken up in chloroform-water, and the chloroform layer was dried and evaporated to yield crude product (24.17 g). Chromatographic purification on silica gel (1000 gel) using ethyl acetate gave 2-[4-[2-(3,4-dimethoxyphenyl)-2-oxoethyl]-1-piperazinyl]-2,4,6-cycloheptatrien-1-one (8.2 g), mp 132°–135° C.

Similarly by replacing 2-bromo-1-(3,4-dimethoxyphenyl)-1-ethanone with 2-bromo-1-[4-(methylsulfonylamino)phenyl]-1-ethanone, 1-phenyl-2-bromo-1-ethanone, 2-bromo-1-(3,4-dimethoxyphenyl)-1-propanone, 2-bromo-1-(3,4,5-trimethoxyphenyl)-1-ethanone, 2-bromo-1-(4-methoxyphenyl)-1-ethanone, 2-bromo-2-butanone, 2-bromo-1-(4-fluorophenyl)-1-ethanone 2-bromo-1-(3-methoxyphenyl)-1-ethanone or 2-bromo-1-(4-hydroxy-3-methoxyphenyl)-1-ethanone, the following compounds of formula VII are obtained respectively: 2-[4-[2-oxo-2-[4-(methylsulfonylamino)phenyl]ethyl]-1-piperazinyl]-2,4,6-cycloheptatrien-1-one: mp 187°–190° C. and nmr(DMSO-d$_6$) δ2.6 (m, 4H), 3.10 (s, 3H), 3.25 (m, 4H), 3.8 (s, 2H), 6.85 (m, 5H), 7.25 (d, 2H) and 7.95 (d, 2H); 2-[4-(2-phenyl-2-oxoethyl)-1-piperazinyl]-2,4,6-cycloheptatrien-1-one; mp 88°–92° C. (crystallized from ethyl acetate) and nmr(CDCl$_3$) δ2.75 (m, 4H), 3.35 (m, 4H), 3.75 (s, 2H) and 7.3 (m, 9H); 2-[4-[2-(3,4-dimethoxyphenyl)-1-methyl-2-oxoethyl]-1-piperazinyl]-2,4,6-cycloheptatrien-1-one: ir(CHCl$_3$) 1652, 1495, 1445 and 1000 cm$^{-1}$ and nmr(CDCl$_3$) δ1.3 (d, 3H), 2.75 (m, 5H), 3.35 (m, 4H), 3.9 (s, 6H) and 7.3 (m, 8H); 2-[4-[2-(3,4,5-trimethoxyphenyl)-2-oxoethyl]-1-piperazinyl]-2,4,6-cycloheptatrien-1-one; 2-[4-[2-(4-methoxyphenyl)-2-oxoethyl]-1-piperazinyl]-2,4,6-cycloheptatrien-1-one, 2-[4-(1methyl-2-oxopropyl)-1-piperazinyl]-2,4,6-cycloheptatrien-1-one; 2-[4-[2-(4-fluorophenyl-2-oxoethyl)-1-piperazinyl]-2,4,6-cycloheptatrien-1-one; 2-[4-[2-(3-methoxyphenyl)-2-oxoethyl]-1-piperazinyl]-2,4,6-cycloheptatrien-1-one; and 2-[4-[2-(4-hydroxy-3-methoxyphenyl)-2-oxoethyl]-1-piperazinyl]-2,4,6-cycloheptatrien-1-one.

To a solution of 2-[4-[2-(3,4-dimethoxyphenyl)-2-oxoethyl]-1-piperazinyl]-2,4,6-cycloheptatrien-1-one (1.33 g, described above) in methanol (20 ml) and chloroform (5 ml), sodium borohydride (0.31 g) was added portionwise over a period of one hr. The solvent was then removed under vacuum. The residue was taken up in chloroform, washed with water, ammonium chloride solution followed by water, dried and evaporated to give the title compound (1.33 g): mp 122°–124° C.; ir(CHCl$_3$) 3420, 1565, 1260 and 1140 cm$^{-1}$; uv max(MeOH) 352 (ε=10040), 256 (ε=15660) and 227 nm (ε=20250); nmr(CDCl$_3$) δ2.6 (m, 6H), 3.3 (m, 4H), 3.85 (s, 6H), 4.7 (m,1H) and 6.8 (m,6H); and Anal. Calcd for C$_{21}$H$_{26}$N$_2$O$_4$: C, 68.08% H, 7.08% N, 7.56% and Found: C, 67.78% H, 7.06% N, 7.36%.

The title compound (3.4 g) was dissolved in methanol containing hydrogen chloride (6 ml of 2N methanolic HCl). The mixture was stirred for 5 min and diethyl ether was gradually added. The precipitated oil was allowed to crystallize and more diethyl ether was added to precipitate all the salt. The mixture was stirred for 20 min and then filtered to yield crude product 3.26 g, mp 165°–168° C. Crystallization from methanol diethyl gave the hydrochloride salt of the title compound: mp 175°–178° C.; ir(nujol) 3300, 2550, 1545 and 1265 cm$^{-1}$; uv max(MeOH) 344 (ε=9025), 252 (ε=27600) and 227 nm(ε=36870); nmr(DMSO-d$_6$)δ3.6 (m, 10H), 3.73 (s, 3H), 3.77 (s, 3H), 5.15 (t, 1H), 6.1 (broad, 1H), 7.0 (m, 8H) and 10.75 (broad, 1H); and Anal. Calcd for C$_{21}$H$_{26}$N$_2$O$_4$HCl: C, 61.84% H, 6.38% N, 6.87% and Found: C, 61.30% H, 6.65% N, 6.78%.

Similarly, by replacing 2-[4-[2-(3,4-dimethoxyphenyl)-2-oxoethyl]-1-piperazinyl]-2,4,6-cycloheptatrien-1-one with an equivalent amount of another compound of formula VII, described above, the following compounds of formula I are obtained respectively, 2-[4-[2-hydroxy-2-[4-(methylsulfonylamino)phenylethyl]-1-piperazinyl]-2,4,6-cycloheptatrien-1-one (I: R$^1$, R$^2$, R$^3$ and R$^5$=H; R$^4$=4-(methylsulfonylamino)phenyl; and Alk=CH): mp 204°–206° C. (crystallized from chloroform-methanol); ir(nujol) 3090, 1610 and 1580 cm$^{-1}$; uv max(MeOH) 351 (ε=10020), 255 (ε=15570) and 229 nm(ε=25100); nmr(DMSO-d$_6$)δ2.6 (4H), 2.95 (s, 3H), 3.25 (m, 6H), 4.7 (m, 1H), 4.9 (s, 1H), 7.0 (m, 9H) and 9.5 (s, 1H); and Anal. Calcd for C$_{20}$H$_{25}$N$_3$O$_4$S: C, 59.55% H, 6.20% N, 10.42% and Found: C, 59.41% H, 6.12% N, 10.49%; 2-[4-(2-hydroxy-2-phenylethyl)-1-piperazinyl-2,4,6-cycloheptatrien-1-one (I: R$^1$, R$^2$, R$^3$ and R$^5$=H; R$^4$=phenyl; and Alk=CH): mp 129°–131° C. (crystallized from methanol-diethyl ether); ir(CHCl$_3$) 3590, 3420 and 1565 cm$^{-1}$; uv max(MeOH) 352 (ε=9550) and 256 nm(ε=15595); nmr(CDCl$_3$)δ2.6 (m, 6H), 3.35 (m, 4H), 3.8 (1H, broad), 4.75 (m, 1H) and 7.0 (m, 10H); and Anal. Calcd for C$_{19}$H$_{22}$N$_2$O$_2$: C, 73.52% H, 7.14% N, 9.03% and Found: C, 73.36% H, 7.01% N, 8.96%; isomer A of 2-[4-[2-hydroxy-1-methyl-2-(3,4-dimethoxyphenyl)ethyl]-1-piperazinyl]-2,4,6-cycloheptatrien-1-one (I: R$^1$, R$^2$ and R$^5$=H; R$^3$=CH$_3$; R$^4$=3,4-dimethoxyphenyl; and Alk=CH): mp 133°–135° C. (crystallized from methanol-diethyl ether); ir(nujol) 3340, 1560, 1260 and 1150 cm$^{-1}$; uv max(MeOH) 352 (ε=9180), 256 (ε=14480) and 229 nm(ε=20700); and nmr(DMSO-d$_6$) δ0.8 (d, 3H), 2.75 (m, 5H), 3.4 (t, 4H), 3.83 (s, 3H), 3.9 (s, 3H), 4.23 (d, 1H), 5.0 (1H, broad) and 6.85 (m, 8H); maleate of isomer B of 2-[4-[2-hydroxy-1-methyl-2-(3,4-dimethoxyphenyl)ethyl]-1-piperazinyl]-2,4,6-cycloheptatrien-1-one (I: R$^1$, R$^2$ and R$^5$=H; R$^3$=CH$_3$; R$^4$=3,4-dimethoxyphenyl; and Alk=CH): mp 165°–168° C. (crystallized from methanol-diethyl ether); ir(nujol) 3420, 2700, 1578, 1550 and 1265 cm$^{-1}$; uv max(MeOH) 343 (ε=9800) and 251 nm(ε=15550); nmr(DMSO-d$_6$) δ1.05 (d, 3H), 3.5 (m, 9H), 3.75 (s, 6H), 5.2 (s, 1H), 6.0 (s, 2H) and 6.9 m, 8H); and Anal. Calcd for C$_{22}$H$_{28}$N$_2$O$_4$·C$_4$H$_4$O$_4$: C, 62.40% H, 6.40% N, 5.60% and Found: C, 62.49% H, 6.46% N, 5.45%; 2-[4-[2-hydroxy-2-(3,4,5-trimethoxyphenyl)ethyl]-1-piperazinyl]-2,4,6-cycloheptatrien-1-one (I: R$^1$, R$^2$, R$^3$ and R$^5$=H; R$^4$=3,4,5-trimethoxyphenyl; and Alk=CH): mp 144.5°–145.5° C. (crystallized from methanol-ethyl acetate); ir(CHCl$_3$) 3600, 3420, 1565 and 1135 cm$^{-1}$; uv max(MeOH) 352 (ε=10150) and 256 nm(ε=15865); nmr(CDCl$_3$) δ3.8 and 3.85 (9H, singlets), 4.7 (s, 1H) and 6.8 (m, 7H); and Anal. Calcd for C$_{22}$H$_{28}$N$_2$O$_5$: C, 65.97% H, 7.05% N, 7.00% and Found: C, 65.77% H, 7.07% N, 6.87%; 2-[4-[2-hydroxy-2-(4-methoxyphenyl)ethyl]-1-piperazinyl]-2,4,6-cycloheptatrien-1-one (I: R$^1$, R$^2$, R$^3$ and R$^5$=H; R$^4$=4-methoxyphenyl; and Alk=CH): mp 139°–140° C. (crystallized from ethyl acetatediethyl ether); ir(CHCl$_3$) 3440, 1565, 1250 and 1175 cm$^{-1}$; uv max(MeOH) 351 (ε=10160), 255 (ε=15635) and 225 nm(ε=23530); nmr(CDCl$_3$) δ2.75 (m, 6H), 3.35 (t, 4H), 3.8 (s, 3H), 4.0 (1H, broad), 4.7 (t, 1H) and 7.0 (m, 9H); and Anal. Calcd for C$_{20}$H$_{23}$N$_2$O$_3$: C, 70.77% H, 6.83% N, 8.26% and Found: C, 70.46% H, 7.20% N, 8.12%; 2-[4-(2-hydroxy-1-methylpropyl)-1-piperazinyl]-2,4,6-cycloheptatrien-1-one (I: R$^1$, R$^3$, R$^4$ and R$^5$=H; R$^2$=CH$_3$; and Alk=CHCH₃): mp 126° C. (crystallized from hexane-ethyl acetate); ir(CHCl₃) 3380 and 1565 cm⁻¹; uv max(-MeOH) 351 ($\epsilon$=9755), 255 ($\epsilon$=14855) and 221 nm($\epsilon$=12135); nmr(CDCl₃) δB 0.95 (d, 3H), 1.15 (d, 3H), 4.25 (1H, broad) and 6.9 (m, 5H); and Anal. Calcd for $C_{15}H_{22}N_2O_2$: C, 68.66% H, 8.45% N, 10.68% and Found: C, 68.85% H, 8.64% N, 10.55%; 2-[4-[2-hydroxy-2-(4-fluorophenyl)ethyl]-1-piperazinyl]-2,4,6-cycloheptatrine-1-one (I: $R^1$, $R^2$, $R^3$ and $R^5$=H; $R^4$=4-fluorophenyl; and Alk=CH): mp 130°-132° C. (crystallized from chloroform-hexane); ir(CHCl₃) 3600, 3440 and 1565 cm⁻¹, uv max(MeOH) 352 ($\epsilon$=9900) and 255 nm($\epsilon$=16500) and nmr(CDCl₃) δ2.65 (m, 7H), 3.35 (t, 4H), 4.7 (m, 1H) and 7.0 (m, 9H); 2-[4-[2-hydroxy-2-(3-methoxyphenyl)ethyl]-1-piperazinyl]-2,4,6-cyclohepta-trien-1-one (I: $R^1$, $R^2$, $R^3$ and $R^5$=H; $R^4$=3 methoxyphenyl; and Alk=CH): mp 105°-107° C. (crystallized from ethyl acetatediethyl ether); ir(CHCl₃) 3600, 3420, 1560, 1260 and 1140 cm⁻¹; uv max(MeOH) 351 ($\epsilon$=9970) and 256 nm($\epsilon$=15450): nmr(CDCl₃) δ2.6 (m, 6H), 3.35 (t, 4H), 3.75 (s, 3H), 4.7 (m, 1H) and 7.0 (m, 9H); and Anal. Calcd for $C_{20}H_{24}N_2O_3$: C, 70.57% H, 7.11% N, 8.23% and Found: C, 70.11% H, 7.21% N, 8.10%; and 2-[4-[2-hydroxy-2-(4-hydroxy-3-methoxy-phenyl)ethyl-1-piperazinyl]-2,4,6-cycloheptatrien-1-one (I: $R^1$, $R^2$, $R^3$ and $R^5$=H; $R^4$=4-hydroxy-3-methoxyphenyl; and Alk=CH): mp 167°-167.5° C. (crystallized from methanol); ir(nujol) 3380, 2900 and 1515 cm⁻¹; uv max(MeOH) 352 ($\epsilon$=10100), 255 ($\epsilon$=15600) and 226 nm($\epsilon$=18600); nmr(DMSO-d₆) δ2.6 (m, 6H), 3.3 (m, 4H), 3.75 (s, 3H), 4.65 (m, 1H), 4.8 (s, 1H), 6.9 (m, 8H) and 3.65 (s, 1H); and Anal. Calcd for $C_{20}H_{24}N_2O_4$: C, 67.40% H, 6.79% N, 7.86% and Found: C, 67.39% H, 6.94% N, 7.82%.

EXAMPLE 5

2-[4-(2-Hydroxyethyl)-3-methyl-1-piperazinyl]-2,4,6-cycloheptatrien-1-one (I: $R^1$=3—CH₃; $R^2$, $R^3$, $R^4$ and $R^5$=H; and Alk=CH)

A solution of 2-methoxy-2,4,6-cycloheptatrien-1-one (6.8 g) and 2-methylpiperazine (5 g) in methanol was refluxed for 16 hr and evaporated. The residue (11 g) was chromatographed on silica gel (250 g) using methanol and the eluate was evaporated to give 7.2 g of 2-(3-methyl-1-piperazinyl)-2,4,6-cycloheptatrien-1-one.

A solution of the latter compound (7.2 g) in methanol (20 ml) was cooled in an ice bath, then ethylene oxide gas (3 g) was introduced. The reaction mixture was kept at 0° C. for 16 hr and evaporated. The residue (5 g) was chromatographed twice on 150 g silica gel with methanol-ethyl acetate (2:8) to yield 3.1 g of the title compound. It was converted to the methane sulfonic acid salt which was crystallized from methanol-acetone to give 1.8 g of methane sulfonate salt of the title compound: mp 136°-138° C.; ir(mull) 3320, 2626 and 1546 cm⁻¹; uv max(MeOH) 343 ($\epsilon$=9460), 251 ($\epsilon$=14090) and 223 nm($\epsilon$=11340); nmr (CDCl₃) δ1.45 (d, 3H), 2.70 (s, 3H), 3.50 (m, 11H), 5.00 (broad, 2H) and 6.9 (m, 5H); and Anal. Calcd for $C_{14}H_{20}N_2O_2 \cdot CH_3SO_3H$: C, 52.30% H, 7.24% N, 8.13% and Found: C, 52.46% H, 7.09% N, 7.91%.

EXAMPLE 6

2-[4-(2-Hydroxypropyl)-1-piperazinyl)-2,4,6-cycloheptatrien-1-one (I: $R^1$, $R^2$, $R^3$, $R^4$ and $R^5$=H and Alk=CHCH₃)

A mixture of 2-(1-piperazinyl)-2,4,6-cycloheptatrien-1-one (12.4 g), described in Example 2), 1-chloro-2-propanone (5.55 g), potassium carbonate (11.04 g) and acetonitrile (120 ml) was refluxed for 4 hr and filtered. Chloroform and water were added to the filtrate. The organic phase was separated, washed with water, dried and evaporated. The residue was chromatographed on silica gel using methanol-ethyl acetate and the eluates were evaporated to give an oil (6.21 g) of 2-[4-(2-oxopropyl)-1-piperazinyl]-2,4,6-cycloheptatrien-1-one (VII; $R^1$, $R^2$, $R^3$ and $R^4$=H and Alk=C—CH₂): ir(CHCl₃) 3660, 3360, 1720, 1710, 1660 and 1560 cm⁻¹; uv max(MeOH) 351 ($\epsilon$=9310), 255 ($\epsilon$=13915) and 221 nm($\epsilon$=11750); nmr(CDCl₃) δ2.12 (s, 3H), 2.62 (t, 4H), 3.21 (s, 2H), 3.35 (s, 4H) and 6.40-7.10 (m, 5H); and Anal. Calcd for $C_{14}H_{18}N_2O_2$: C, 68.26% H, 7.37% N, 11.37% and Found: C, 67.33% H, 7.59% N, 11.44%.

A solution of the latter compound (12.0 g) in methanol (100 ml) was cooled in an ice-bath, then sodium borohydride was added in portions and the progress of the reduction was monitored by tlc. When the reaction was complete the solvent was evaporated, and the residue was dissolved in water. It was extracted with chloroform, dried over sodium sulfate and evaporated to yield 9.1 g of crude product. Chromatographic purification on 350 g silica gel with methanol-ethyl acetate (1:9) afforded 7.0 g of a residue which after two crystallizations from ethyl acetate yielded 4.0 g of the title compound: mp 92°-93° C.; ir(CHCl₃) 3450 and 1565 cm⁻¹; uv max(MeOH) 353 ($\epsilon$=9870), 225 ($\epsilon$=7263) and 221 nm($\epsilon$=5785); nmr(CDCl₃) δ1.13 (d, 3H), 2.6 (m, 6H), 3.35 (t, 4H), 3.75 (t, 4H), 3.75 (m, 1H) and 6.8 (m, 5H); and Anal. Calcd for $C_{14}H_{20}N_2O_2$: C, 67.71% H, 8.21% N, 11.28% and Found: C, 67.81% H, 8.18% N, 11.60%.

EXAMPLE 7

2-[4-[2-Hydroxy-2-(3,4-dimethoxyphenyl)ethyl]-1-piperazinyl]-2,4,6-cycloheptatrien-1-one (I: $R^1$, $R^2$, $R^3$ and $R^5$=H; $R^4$=3,4-dimethoxyphenyl and Alk=CH)

Sodium carbonate (18.84 g) and water (41.4 ml) was added to a stirring suspension at 0° to 5° C. of 2-bromo-1-(3,4-dimethoxyphenyl)-1-ethanone (32.03 g, described in Example 4) and 1-benzylpiperazine (24 ml) in acetonitrile (90 ml). The suspension was stirred at room temperature for 2.5 hr and evaporated. The residue was dissolved in a mixture of water and chloroform, and the chloroform layer was dried and evaporated. Chromatographic purification on silica gel (700 g) using ethyl acetate-hexane (60:1 to 100:1) gave 32 g of 2-(4-benzyl-1-piperazinyl)-1-(3,4-dimethoxyphenyl)-1-ethanone, nmr(CDCl₃) δ2.65, 3.57, 3.74, 3.89, 3.91, 6.81, 7.37 and 7.53.

A suspension of the latter compound (32 g), 10% palladium on carbon (8.22 g), 2N hydrogen chloride in methanol (40.58 ml) and methanol (345 ml) was stirred rapidly under an atmosphere of hydrogen for 24 hr and filtered. The filtrate was washed with chloroform and basified with 20% sodium hydroxide (20 ml). The resulting solution was extracted with chloroform and the extract was dried and evaporated to give 22.41 g of 2-(1-piperazinyl)-1-(3,4-dimethoxyphenyl)-1-ethanone, nmr(CDCl₃) δ2.12, 2.55, 2.90, 3.70, 3.92, 6.82 and 7.60.

To a solution at room temperature of the latter compound (22.4 g) in methanol (120 g), sodium borohydride (4.46 g) was slowly added. The solution was evaporated and the residue was dissolved in a mixture of water and chloroform. The chloroform phase was separated, dried and evaporated to give 16.65 g of 2-(1-piperazinyl)-1-

(3,4-dimethoxyphenyl)-1-ethanol, nmr(CDCl₃) δ2.4 (m, 4H), 2.6 (m, 2H), 2.9 (t, 4H), 3.82 and 3.85 (singlets, 6H), 4.65 (m, 1H) and 6.85 (m, 3H).

A solution of the latter compound (0.728 g), 2-methoxy-2,4,6-cycloheptatrien-1-one (0.048 g), methanol (5 ml) and sodium (0.070 g) in methanol (2.9 ml) was stirred at 70° C. for one hr, at room temperature for 20 hr and at 80° C. for one hr and evaporated. The residue was dissolved in a solution of water and chloroform. The chloroform phase was separated, dried, evaporated (1.25 g of residue) and crystallized from chloroform-hexane to give the title compound, mp 120°–123° C. and nmr(CDCl₃) δ2.7 (m, 6H), 3.35 (t, 4H), 3.85 and 3.9 (singlets, 6H), 4.7 (t, 1H) and 6.8 (m, 8H). The title compound of this example is identical to the title compound of Example 4.

EXAMPLE 8

Resolution of 2-[4-[2-Hydroxy-2-(3,4-dimethoxyphenyl)ethyl]-1-piperazinyl]-2,4,6-cycloheptatrien-1-one A solution of 2-[4-[2-hydroxy-2-(3,4-dimethoxyphenyl)ethyl]-1-piperazinyl]-2,4,6-cycloheptatrien-1-one (3.7 g, described in Example 4) and L-ditoluyltartaric acid (4.24 g) in methanol was stirred at room temperature overnight and filtered. Diethyl ether (15 ml) was added to the filtrate and the solution was filtered. The above two collected precipitates were combined (7.3 g, mp 178°–180° C.), methanol (150 ml) was added and the mixture was refluxed for 5 to 10 min, cooled to room temperature and filtered to give solid A (3.5 g, mp 195°–197° C.) and filtrate B. Solid A was washed with boiling methanol (30 ml) to give a solid (3.45 g) of the salt of (+)-2-[4-[2-hydroxy-2-(3,4-dimethoxyphenyl)-ethyl]-1-piperazinyl]-2,4,6-cycloheptatrien-1-one with L-ditoluyltaric acid; mp 197°–199° C. and $[\alpha]_D^{25}+45.8°$ (c=1, dimethylformamide). A suspension of the latter salt in water was basified with aqueous 10% sodium hydroxide and extracted with ethyl acetate. The extract was evaporated and crystallized from hexane-chloroform to obtain the optical (±)-isomer (1.1 g) of the title compound; mp 124°–125° C., and $[\alpha]_D^{25}+11.7°$ (c=1, dimethylformamide).

The above filtrate B was evaporated. A suspension of the residue in water was basified with aqueous 10% sodium hydroxide and extracted with ethyl acetate. The extract was evaporated to give a residue (1.6 g) which was treated with a solution of D-ditoluyltartaric acid (1.67 g) in methanol (7 ml) at room temperature overnight. The precipitate (2.92 g) was collected to give the salt of (−)-2-[4-[2-hydroxy-2-(3,4-dimethoxyphenyl)ethyl]-1-piperazinyl]-2,4,6-cycloheptatrien-1-one with D-ditoluyltartaric acid: mp 193°–195° C., and $[\alpha]_D^{25}-45.0°$ (c=1, dimethylformamide). A suspension of the latter salt in water was basified with aqueous 10% sodium hydroxide and extracted with ethyl acetate. The extract was evaporated and crystallized from hexane-chloroform to obtain the optical-(−)-isomer of the title compound; mp 122°–124° C., and $[\alpha]_D^{25}-12.0°$ (c=1, dimethylformamide).

Similarly, by replacing 2-[4-[2-hydroxy-2-(3,4-dimethoxyphenyl)ethyl]-1-piperazinyl]-2,4,6-cycloheptatrien-1-one with isomer B of 2-[4-[2-hydroxy-1-methyl-2-(3,4-dimethoxyphenyl)-ethyl]-1-piperazinyl]-2,4,6-cycloheptatrien-1-one (described in Example 4), the following optical isomers of this compound were obtained: optical (+) isomer, mp 96°–98° C. (crystallized from ethyl acetate-diethyl ether) and $[\alpha]_D^{25}+84.2°$ (c=1, dimethylformamide); maleate salt of optical (+) isomer, mp 161°–163° C. (crystallized from methanol-diethyl ether) and $[\alpha]_D^{25}+37.4°$ (c=1, dimethylformamide); optical (−) isomer, mp 95°–98° C. (crystallized from ethyl acetate-diethyl ether) and $[\alpha]_D^{25}-82.5°$ (c=1, dimethylformamide); and maleate salt of optical (−) isomer, mp 160°–162° C. (crystallized from methanol-diethyl ether) and $[\alpha]_D^{25}-36.5°$ (c=1, dimethylformamide).

We claim:

1. A compound of the formula

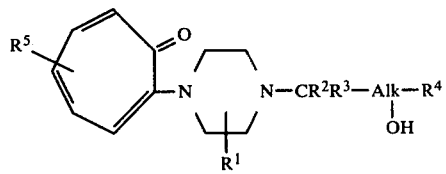

in which Alk is a trivalent alkylene having one to six carbon atoms; $R^1$ is hydrogen or lower alkyl having one to three carbon atoms; $R^2$ and $R^3$ each is hydrogen or lower alkyl having one to three carbon atoms; $R^4$ is hydrogen, phenyl, hydroxy, phenoxy, phenyl mono-, di- or trisubstituted with methylsulfonylamino, lower alkyl, halo, lower alkoxy, hydroxy or trifluoromethyl, or phenoxy mono-, di- or trisubstituted with lower alkyl, halo, lower alkoxy, hydroxy or trifluoromethyl; and $R^5$ represents a substituent at positions 3,4,5,6 or 7 of the 2,4,6-cycloheptatrien-1-one ring and is selected from hydrogen, halo, lower alkyl, lower alkoxy, trifluoromethyl, or 1-oxo(lower)alkylamino; with the proviso that when $R^4$ is hydroxy, the hydroxy groups are joined to different carbon atoms; or a therapeutically acceptable acid addition salt thereof.

2. A compound of claim 1 in which $R^1$ is hydrogen or methyl; $R^2$ and $R^3$ each is hydrogen or lower alkyl having one to three carbon atoms, $R^4$ is hydrogen, phenyl, hydroxy, phenoxy, phenyl mono-, di- or trisubstituted with methylsulfonylamino, lower alkoxy or hydroxy, or phenoxy mono-, di- or trisubstituted with lower alkyl or halo; and $R^5$ represents a substituent at position 7 of the 2,4,6-cycloheptatrien-1-one ring and is selected from hydrogen, halo, lower alkyl, lower alkoxy, trifluoromethyl, or 1-oxo(lower)alkylamino; or a therapeutically acceptable acid addition salt thereof.

3. A compound of claim 1 in which Alk is a trivalent alkylene having one to three carbon atoms; $R^1$ is hydrogen; $R^2$ and $R^3$ each is hydrogen or lower alkyl having one to three carbon atoms; $R^4$ is hydrogen, phenyl, hydroxy, phenoxy, phenyl mono-, di- or trisubstituted with lower alkoxy or hydroxy, or phenoxy monosubstituted with lower alkyl; or halo; $R^5$ represents a substituent at position 7 of the 2,4,6-cycloheptatrien-1-one ring and is selected from hydrogen or bromo; or a therapeutically acceptable acid addition salt thereof.

4. A compound of claim 1 in which Alk is CH; $R^1$, $R^2$ and $R^5$ are hydrogen; $R^3$ is hydrogen or lower alkyl having one to three carbon atoms; and $R^4$ is phenyl or phenyl mono-, di- or trisubstituted at positions 3, 4 or 5 with lower alkoxy or hydroxy; or a therapeutically acceptable acid addition salt thereof.

5. 4-(2-Oxo-3,5,7-cycloheptatrien-1-yl)-1-piperazineethanol, a compound of claim 1 wherein $R^1$, $R^2$, $R^3$, $R^4$ and $R^5$ are hydrogen and Alk is CH.

6. 2-[4-(3-Hydroxypropyl)-1-piperazinyl]-2,4,6-cycloheptatrien-1-one, a compound of claim 1 wherein $R^1$, $R^2$, $R^3$, $R^4$ and $R^5$ are hydrogen and Alk is $CH_2CH$.

7. 2-[4-[2-Hydroxy-2-(3,4-dimethoxyphenyl)ethyl]-1-piperazinyl]-2,4,6-cycloheptatrien-1-one, a compound of claim 1 wherein $R^1$, $R^2$, $R^3$ and $R^5$ are hydrogen; $R^4$ is 3,4-dimethoxyphenyl; and Alk is CH.

8. (+)-2-[4-[2-Hydroxy-2-(3,4-dimethoxyphenyl)ethyl]-1-piperazinyl]-2,4,6-cycloheptatrien-1-one having $[\alpha]_D^{25} +11.7°$ (c=1, dimethylformamide), a compound of claim 7.

9. (−)-2-[4-[2-Hydroxy-2-(3,4-dimethoxyphenyl)ethyl]-1-piperazinyl]-2,4,6-cycloheptatrien-1-one having $[\alpha]_D^{25} -12.0°$ (c=1, dimethylformamide), a compound of claim 7.

10. 2-[4-[2-Hydroxy-2-[4-(methylsulfonylamino)phenyl]ethyl]-1-piperazinyl]-2,4,6-cycloheptatrien-1-one, a compound of claim 1 wherein $R^1$ $R^2$, $R^3$ and $R^5$ are hydrogen; $R^4$ is 4-(methylsulfonylamino)phenyl; and Alk is CH.

11. 2-[4-[3-[4-(1,1-Dimethylethyl)phenoxy]-2-hydroxypropyl]-1-piperazinyl]-2,4,6-cycloheptatrien-1-one, a compound of claim 1 wherein $R^1$, $R^2$, $R^3$ and $R^5$ are hydrogen; $R^4$ is 4-(1,1-dimethylethyl)phenoxy; and Alk is $CHCH_2$.

12. 2-[4-[3-(4-Chlorophenoxy)-2-hydroxypropyl]-1-piperazinyl]-2,4,6-cycloheptatrien-1-one, a compound of claim 1 wherein $R^1$, $R^2$, $R^3$ and $R^5$ are hydrogen; $R^4$ is 4-chlorophenoxy; and Alk is $CHCH_2$.

13. 2-[4-(2-Hydroxyethyl)-3-methyl-1-piperazinyl]-2,4,6-cycloheptatrien-1-one, a compound of claim 1 wherein $R^1$ is 3-methyl; $R^2$, $R^3$, $R^4$ and $R^5$ are hydrogen; and Alk is CH.

14. 2-[4-(2-Hydroxypropyl)-1-piperazinyl]-2,4,6-cycloheptatrien-1-one, a compound of claim 1 wherein $R^1$, $R^2$, $R^3$, $R^4$ and $R^5$ are hydrogen; and Alk is $CHCH_3$.

15. 2-[4-[2-Hydroxy-2-(3,4,5-trimethoxyphenyl)ethyl]-1-piperazinyl]-2,4,6-cycloheptatrien-1-one, a compound of claim 1 wherein $R^1$, $R^2$, $R^3$ and $R^5$ are hydrogen; $R^4$ is 3,4,5-trimethoxyphenyl; and Alk is CH.

16. 2-[4-[2-Hydroxy-2-(3,4-dimethoxyphenyl)ethyl]-1-piperazinyl]-2,4,6-cycloheptatrien-1-one hydrochloride, a compound of claim 1 wherein $R^1$, $R^2$, $R^3$ and $R^5$ are hydrogen; $R^4$ is 3,4-dimethoxyphenyl; and Alk is CH, and acid addition salt is the hydrochloride.

17. 2-[4-(2-Hydroxy-2-phenylethyl)-1-piperazinyl]-2,4,6-cycloheptatrien-1-one, a compound of claim 1 wherein $R^1$, $R^2$, $R^3$ and $R^5$ are hydrogen; $R^4$ is phenyl; and Alk is CH.

18. 2-[4-[2-Hydroxy-1-methyl-2-(3,4-dimethoxyphenyl)ethyl]-1-piperazinyl]-2,4,6-cycloheptatrien-1-one, a compound of claim 1 wherein $R^1$, $R^2$ and $R^5$ are hydrogen; $R^3$ is methyl; $R^4$ is 3,4-dimethoxyphenyl; and Alk is CH.

19. 2-[4-[2-Hydroxy-1-methyl-2-(3,4-dimethoxyphenyl)ethyl]-1-piperazinyl]-2,4,6-cycloheptatrien-1-one, having mp 133°–135° C., a compound of claim 18.

20. 2-[4-[2-Hydroxy-1-methyl-2-(3,4-dimethoxyphenyl)ethyl]-1-piperazinyl]-2,4,6-cycloheptatrien-1-one, the maleate salt thereof having mp 165°–168° C., a compound of claim 18.

21. (+)-2-[4-[2-Hydroxy-1-methyl-2-(3,4-dimethoxyphenyl)ethyl]-1-piperazinyl]-2,4,6-cycloheptatrien-1-one, having $[\alpha]_D^{25} +84.2°$ (c=1, dimethylformamide), a compound of claim 20.

22. (−)-2-[4-[2-Hydroxy-1-methyl-2-(3,4-dimethoxyphenyl)ethyl]-1-piperazinyl]-2,4,6-cycloheptatrien-1-one, having $[\alpha]_D^{25} -82.5°$ (c=1, dimethylformamide), a compound of claim 20.

23. 2-[4-[1-(Hydroxymethyl)ethyl]-1-piperazinyl]-2,4,6-cycloheptatrien-1-one, a compound of claim 1 wherein $R^1$, $R^3$, $R^4$ and $R^5$ are hydrogen; $R^2$ is methyl; and Alk is CH.

24. 2-[4-(2-Hydroxy-1-methylpropyl)-1-piperazinyl]-2,4,6-cycloheptatrien-1-one, a compound of claim 1 wherein $R^1$, $R^2$, $R^4$ and $R^5$ are hydrogen; $R^3$ is methyl; and Alk is $CHCH_3$.

25. 2-[4-[2-Hydroxy-2-(4-methoxyphenyl)ethyl]-1-piperazinyl]-2,4,6-cycloheptatrien-1-one, a compound of claim 1 wherein $R^1$, $R^2$, $R^3$ and $R^5$ are hydrogen; $R^4$ is 4-methoxyphenyl; and Alk is CH.

26. 2-[4-[2-Hydroxy-2-(4-fluorophenyl)ethyl]-1-piperazinyl]-2,4,6-cycloheptatrien-1-one, a compound of claim 1 wherein $R^1$, $R^2$, $R^3$ and $R^5$ are hydrogen; $R^4$ is 4-fluorophenyl; and Alk is CH.

27. 2-[4-(2,3-Dihydroxypropyl)-1-piperazinyl]-2,4,6-cycloheptatrien-1-one, a compound of claim 1 wherein $R^1$, $R^2$, $R^3$ and $R^5$ are hydrogen; $R^4$ is hydroxy; and Alk is $CHCH_2$.

28. 2-[4-[2-Hydroxy-2-(3-methoxyphenyl)ethyl]-1-piperazinyl]-2,4,6-cycloheptatrien-1-one, a compound of claim 1 wherein $R^1$, $R^2$, $R^3$ and $R^5$ are hydrogen; $R^4$ is 3-methoxyphenyl; and Alk is CH.

29. 2-[4-[2-Hydroxy-2-(4-hydroxy-3-methoxyphenyl)ethyl]-1-piperazinyl]-2,4,6-cycloheptatrien-1-one, a compound of claim 1 wherein $R^1$, $R^2$, $R^3$ and $R^5$ are hydrogen; $R^4$ is 4-hydroxy-3-methoxyphenyl; and Alk is CH.

30. A pharmaceutical composition, for stimulating dopamine receptors in a mammal in need thereof, which comprises an effective dopamine receptor stimulating amount of a compound of the formula

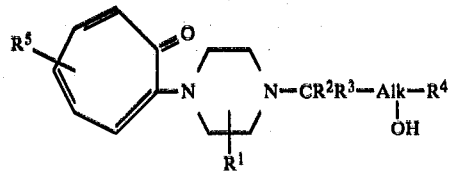

in which Alk is a trivalent alkylene having one to three carbon atoms; $R^1$ is hydrogen; $R^2$ and $R^3$ each is hydrogen or lower alkyl having one to three carbon atoms; $R^4$ is hydrogen, phenyl, hydroxy, phenoxy, phenyl mono-, di- or trisubstituted with lower alkoxy or hydroxy, or phenoxy monosubstituted with lower alkyl or halo; $R^5$ represents a substituent at position 7 of the 2,4,6-cycloheptatrien-1-one ring and is selected from hydrogen or bromo; or a therapeutically acceptable acid addition salt thereof, and a pharmaceutically acceptable carrier therefor.

31. A pharmaceutical composition, for stimulating dopamine receptors in a mammal in need thereof, comprising an effective dopamine receptor stimulating amount of a compound of the formula

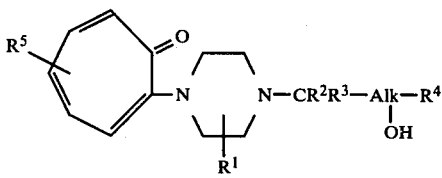

which Alk is a trivalent alkylene having one to three carbon atoms; $R^1$ is hydrogen; $R^2$ and $R^3$ each is hydrogen or lower alkyl having one to three carbon atoms; $R^4$ is hydrogen, phenyl, hydroxy, phenoxy, phenyl mono-, di- or trisubstituted with lower alkoxy or hydroxy, or phenoxy monosubstituted with lower alkyl or halo; $R^5$ represents a substituent at position 7 of the 2,4,6-cycloheptatrien-1-one ring and is selected from hydrogen or bromo; or a therapeutically acceptable acid addition salt thereof, and an agent selected from bromocriptine, lergotrile, levodopa, combination of levodopa and carbidopa, L-prolyl-L-leucylglycinamide and L-prolyl-N-methyl-D-leucylglycinamide.

32. The pharmaceutical composition of claim 30 or 31 wherein said compound is selected from 2-[4-[2-hydroxy-1-methyl-2-(3,4-dimethoxyphenyl)ethyl]-1-piperazinyl]-2,4,6-cycloheptatrien-1-one and 2-[4-[2-hydroxy-2-(3,4-dimethoxyphenyl)ethyl]-1-piperazinyl]-2,4,6-cycloheptatrien-1-one, or a therapeutically acceptable acid addition salt thereof.

33. A method of stimulating dopamine receptors in a mammal in need thereof, which comprises administering to said mammal an effective dopamine receptor stimulating amount of a composition of claim 30, in combination with an effective amount of an agent selected from bromocriptine lergotrile, levodopa, combination of levodopa and carbidopa, L-prolyl-L-leucylglycinamide and L-prolyl-N-methyl-D-leucylglycinamide.

34. The method of treating disorders in a mammal, which disorders respond to dopamine-receptor stimulation, which method comprises administering to said mammal an effective dopamine receptor stimulating amount of a composition of claim 30.

35. A method of stimulating dopamine receptors in a mammal in need thereof, which comprises administering to said mammal an effective dopamine receptor stimulating amount of a composition of claim 30.

36. The method of claim 33 wherein the composition of claim 44, and said agent are administered sequentially or simultaneously.

37. The method of claim 35 wherein the composition contains a compound selected from 2-[4-[2-hydroxy-1-methyl-2-(3,4-dimethoxyphenyl)ethyl]-1-piperazinyl]-2,4,6-cycloheptatrien-1-one and 2-[4-[2-hydroxy-2-(3,4-dimethoxyphenyl)ethyl]-1-piperazinyl]-2,4,6-cycloheptatrien-1-one, or a therapeutically acceptable acid addition salt thereof.

* * * * *